United States Patent
Lin et al.

(10) Patent No.: US 10,426,811 B2
(45) Date of Patent: Oct. 1, 2019

(54) BANANA FERMENTATION PRODUCT AND MANUFACTURING METHOD AND USE OF THE SAME

(71) Applicant: TCI CO., LTD., Taipei (TW)

(72) Inventors: Yung-Hsiang Lin, Taipei (TW); Po-Chun Hsu, Taipei (TW); Cheng-Yu Ho, Taipei (TW)

(73) Assignee: TCI CO., LTD., Taipei (TW)

(*) Notice: Subject to any disclaimer, the term of this patent is extended or adjusted under 35 U.S.C. 154(b) by 7 days.

(21) Appl. No.: 15/685,915

(22) Filed: Aug. 24, 2017

(65) Prior Publication Data

US 2018/0055905 A1    Mar. 1, 2018

Related U.S. Application Data

(60) Provisional application No. 62/379,427, filed on Aug. 25, 2016.

(30) Foreign Application Priority Data

Jan. 11, 2017  (TW) .............................. 106100871 A

(51) Int. Cl.
| | |
|---|---|
| *A61K 36/88* | (2006.01) |
| *A23L 2/02* | (2006.01) |
| *A23L 2/52* | (2006.01) |
| *A23L 2/38* | (2006.01) |
| *A23L 11/00* | (2016.01) |
| *A23L 33/105* | (2016.01) |

(52) U.S. Cl.
CPC ................ *A61K 36/88* (2013.01); *A23L 2/02* (2013.01); *A23L 2/382* (2013.01); *A23L 2/52* (2013.01); *A23L 11/09* (2016.08); *A23L 33/105* (2016.08); *A23V 2002/00* (2013.01); *A23Y 2240/75* (2013.01); *A61K 2236/19* (2013.01); *Y02A 50/473* (2018.01)

(58) Field of Classification Search
CPC ... A61K 36/88; A23L 2/02; A23L 2/52; A23L 2/382
See application file for complete search history.

(56) References Cited

PUBLICATIONS

Konate et al., Journal of Food Research; vol. 4, No. 2; 2015.*
Aegerter et al,. Applied and Environmental Microbiology, May 1980, pp. 937-942, vol. 39, No. 5.*

* cited by examiner

*Primary Examiner* — Ruth A Davis
(74) *Attorney, Agent, or Firm* — Christensen, Fonder, Dardi & Herbert PLLC

(57) ABSTRACT

The present invention provides a banana fermentation product, which is obtained by subjecting a banana pulp juice to a pre-fermentation and then a post-fermentation, wherein the pre-fermentation is conducted in the presence of *Streptococcus thermophiles* and yeast and the post-fermentation is conducted in the presence of *Acetobacter*. The banana fermentation product of the present invention is effective in anti-oxidation, increasing the amount of probiotics in the intestinal tract, reducing the amount of bad bacteria in the intestinal tract, and relieving constipation symptoms. The banana fermentation product of the present invention can further be used for providing an edible composition or a pharmaceutical composition.

11 Claims, 5 Drawing Sheets

BANANA FERMENTATION PRODUCT AND MANUFACTURING METHOD AND USE OF THE SAME

RELATED APPLICATIONS

This application claims priority to U.S. Provisional Application Ser. No. 62/379,427 filed on Aug. 25, 2016, in the United States Patent and Trademark Office, and to Taiwan Patent Application No. 106100871 filed on Jan. 11, 2017, in the Taiwan Intellectual Property Office, the disclosures of which are incorporated herein in their entirety by reference.

FIELD OF THE INVENTION

The present invention provides a banana fermentation product, especially a banana fermentation product that is effective in anti-oxidation, increasing the amount of probiotics and reducing the amount of bad bacteria in the intestinal tract, and relieving constipation symptoms.

BACKGROUND OF THE INVENTION

Banana is a monocotyledonous plant of large herbs and belongs to the family Musaceae. The places of origin of bananas include southern China, India, West Indies, and Oceania. Taiwan is located in the subtropics and its banana productivity is abundant. Taiwan has been known as the kingdom of banana because it grows all year round and is produced abundantly from May to August. Banana contains many nutrients, such as carbohydrates, starch, vitamins, pectin, calcium, phosphorum, ferrum and various enzymes.

About 80% people would more or less experience constipation throughout their lives. Constipation may be caused by many reasons including insufficient intake of cellulose and water, long-term sedentary, and environmental changes, and could become serious as being pregnant, traveling and changing diets. Constipation could be the syndrome of other rare diseases such as scleroderma, nervous system and endocrine system diseases (including thyroid diseases, multiple sclerosis, Parkinson's disease, stroke, and spinal cord injury). Colon inertia that is caused by unknown reasons may prolong gastric emptying time, lead to anal sphincter disorder, and disable people from feeling relaxed during bowel movement, and thus, may also cause constipation.

Most patients with constipation can be treated by increasing high-fiber food products and water in their diets. Banana, which is common and abundant in Taiwan, is used in the present invention for producing a banana fermentation product via a fermentation process in the presence of specific microbes. The banana fermentation product provides effects much better than banana on preventing constipation. Therefore, the banana fermentation product can be used for providing an edible composition or a pharmaceutical composition for relieving constipation symptoms via a natural, non-chemical synthesis process without causing side effects.

SUMMARY OF THE INVENTION

Accordingly, the present invention provides a banana fermentation product, which is obtained by subjecting a banana pulp juice to a pre-fermentation and then a post-fermentation, wherein the pre-fermentation is conducted in the presence of *Streptococcus thermophilus* and yeast and the post-fermentation is conducted in the presence of *Acetobacter*.

The present invention further provides a use of the banana fermentation product for relieving constipation symptom(s).

The present invention still further provides a use of the banana fermentation product for increasing the amount of probiotics in the intestinal tract.

The present invention yet further provides a use of the banana fermentation product for reducing the amount of bad bacteria in the intestinal tract.

The present invention still yet further provides a use of the banana fermentation product for anti-oxidation.

The present invention yet still provides a method for manufacturing a banana fermentation product, comprising subjecting a banana pulp juice to a pre-fermentation and then a post-fermentation, wherein the pre-fermentation is conducted in the presence of *Streptococcus thermophilus* and yeast, and the post-fermentation is conducted in the presence of *Acetobacter*.

In one embodiment of the present invention, the *Streptococcus thermophilus* is DSMZ 28121 strain, the yeast is *Saccharomyces cerevisiae* ATCC 4126T strain, and the *Acetobacter* is at least one of *Acetobacter aceti* TISTR 102 strain and *Acetobacter aceti* DSMZ 3508 strain.

In one embodiment of the present invention, the constipation symptom to be relieved includes at least one of hard stool, little stool amount, hard bowel movement, incomplete bowel movement, stomach bloating, and decreased frequency of bowel movement.

In one embodiment of the present invention, the probiotic is at least one of *Lactobacillus acidophilus*, *Lactobacillus rhamnosus*, *Lactobacillus plantarum*, *Lactobacillus gasseri*, and *Lactobacillus brevis*.

In one embodiment of the present invention, the bad bacterium is *Escherichia coli*.

Therefore, the present invention provides a banana fermentation product, which is obtained by subjecting a banana pulp juice to a pre-fermentation and then a post-fermentation, wherein the pre-fermentation is conducted in the presence of *Streptococcus thermophilus* TCI 633 (DSMZ 28121) and *Saccharomyces cerevisiae* (ATCC 4126T) and the post-fermentation is conducted in the presence of at least one of *Acetobacter aceti* (TISTR 102) and *Acetobacter aceti* (DSMZ 3508). The banana fermentation product thus obtained is effective in anti-oxidation, increasing the amount of probiotics in the intestinal tract, reducing the amount of bad bacteria in the intestinal tract, and relieving constipation symptoms, and thus, can be used for providing a pharmaceutical composition or an edible composition.

The above descriptions, however, are only directed to the preferable examples of the present invention, and not be provided for limiting the scope of the present invention. Without departing from the spirit and scope of the present invention, people skilled in the art may proceed with a variety of modifications and changes based on the disclosures and suggestions of the invention as described, and all such modifications and changes should be intended to be included within the scope of the appended claims.

DESCRIPTION OF THE PREFERRED EMBODIMENTS

The present invention provides a banana fermentation product, which is prepared by subjecting a banana pulp juice to a fermentation in the presence of microbes. In addition to the trace elements contained in the banana itself, the banana fermentation product in accordance with the present invention also contains antioxidants (e.g., superoxide dismutase (SOD)) and organic acids produced during the process of fermentation, and thus, is effective in increasing the amount of probiotics and reducing the amount of bad bacteria in the intestinal tract, so as to maintain the environment of the intestinal tract, facilitate bowel movement, relieve constipation symptoms, and alleviate stomach bloating and abdominal pain.

Example 1: Preparation of Banana Fermentation Product

In the preferable embodiment of the present invention, a banana pulp was mixed with distilled water by a ratio ranging from 1:0.8 to 1:1.2 (banana pulp:distilled water). In one embodiment of the present invention, 100 g banana pulp was mixed with 100 g distilled water to provide a banana pulp juice, which is used as an empty medium. The empty medium was sterilized by pasteurization, and then *Streptococcus thermophilus* TCI 633 (DSMZ 28121) and *Saccharomyces cerevisiae* (ATCC 4126T) were inoculated therein. The mixture thus obtained was subjected to a pre-fermentation at a constant temperature of 30° C.±1° C. for 72 hours. After the pre-fermentation was complete, *Acetobacter aceti* (TISTR 102) or *Acetobacter aceti* (DSMZ 3508) was added directly thereto, followed by a post-fermentation at a constant temperature of 30° C.±1° C. for 21 days, to provide a banana fermentation product of the present invention.

Example 2: Measurement of the Content of SOD-Like in the Banana Fermentation Product of the Present Invention Superoxide dismutase (SOD) is an enzyme which catalyzes the dismutation of superoxide free radicals to produce oxygen and hydrogen peroxide, and thus, can provide an antioxidant effect on cells being exposed to oxygen. In this experimentation, a SOD activity kit (purchased from Enzo Life Science, CAT number # ADI-900-157) was used to analyze the oxidative stress of cells. Results are shown in FIG. 1.

Figure 1:
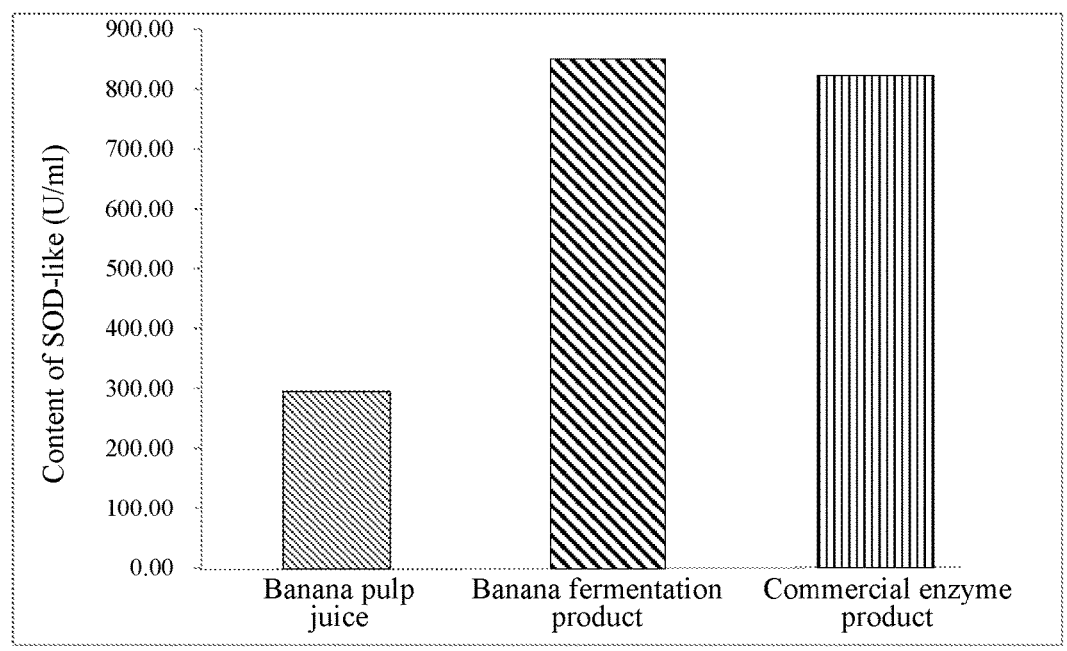
FIG. 1 is a diagram showing the content of superoxide dismutase-like (SOD-like) in a banana pulp juice (i.e., the control group), the banana fermentation product of the present invention, and a commercial enzyme product.

As shown in FIG. 1, as compared to a commercial enzyme product (i.e., a plant enzyme) and a banana pulp juice (i.e., the control group), the content of the SOD-like in the banana fermentation product of the present invention was significantly higher. These results indicate that the banana fermentation product of the present invention has a higher SOD activity, and thus, can effectively enhance the defense against oxidative stress.

Figure 2:
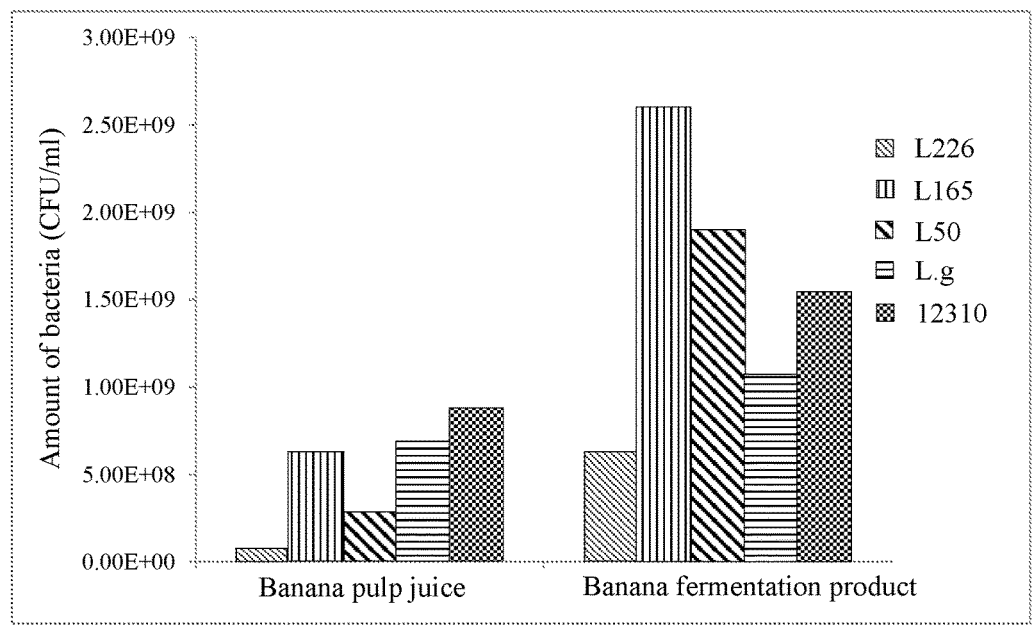
FIG. 2 is a diagram showing the effect of the banana fermentation product of the present invention on increasing the amount of probiotics in the intestinal tract.

Example 3: Effects of the Banana Fermentation Product of the Present Invention on Increasing the Amount of Probiotics and Reducing the Amount of Bad Bacteria in the Intestinal Tract Probiotics (probiotic bacteria) is a microbe, whose strains, mixed strains, extracts or metabolites have positive effects on the hosts. Probiotics are usually living bacterium originating from inside the human body that are beneficial for the health of the intestinal tract. In this experimentation, five common types of probiotics in the intestinal tract, including *Lactobacillus acidophilus* (L226 strain), *Lactobacillus rhamnosus* (L165 strain), *Lactobacillus plantarum* (L50 strain), *Lactobacillus gasseri* (L.g strain) and *Lactobacillus brevis* (12310 strain), were respectively cultivated in a MRS medium with the banana fermentation product of the present invention at 37° C. for 15 hours, followed by conducting a colony counting. Results are shown in FIG. 2. As shown in FIG. 2, as compared to the banana pulp juice (i.e., a juice obtained by mixing banana pulp with distilled water by a ratio ranging from 1:0.8 to 1:1.2 (banana pulp:distilled water)), the banana fermentation product of the present invention can increase the amount of probiotics by 4 to 8 fold.

Figure 3:
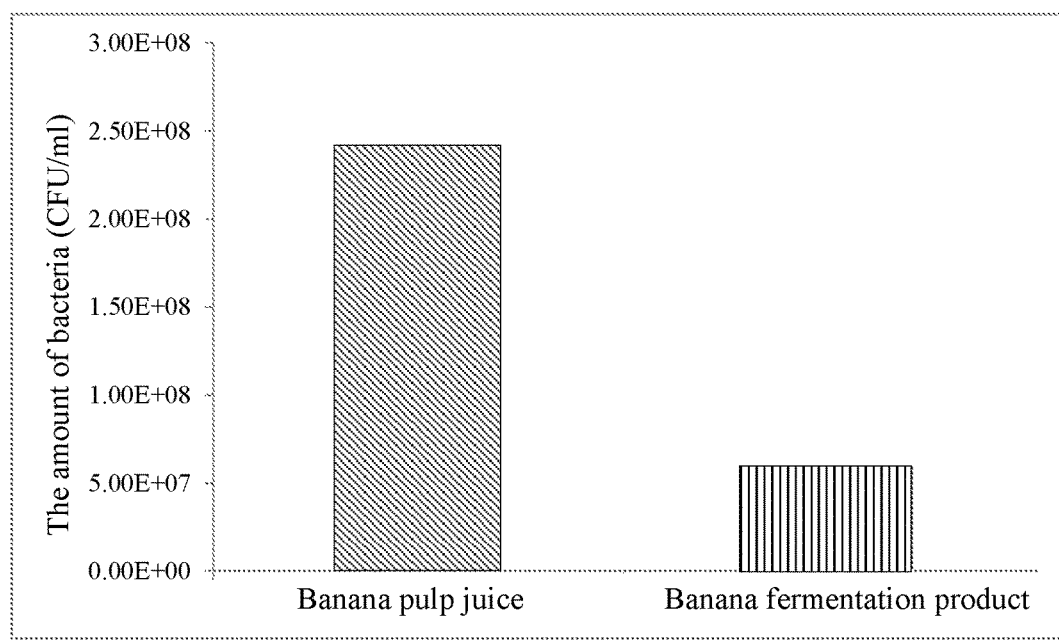
FIG. 3 is a diagram showing the effect of the banana fermentation product of the present invention on reducing the amount of *Escherichia coli* in the intestinal tract.

In this experimentation, *Escherichia coli* (i.e., a bad bacterium in the intestinal tract) was also cultivated in an MRS medium added with the banana fermentation product at 37° C. for 15 hours, followed by conducting a colony counting. Results are shown in FIG. 3. As shown in FIG. 3, as compared to the banana pulp juice, the banana fermentation product of the present invention can reduce the amount of *Escherichia coli* by 4 fold. These results indicate that the banana fermentation product of the present invention is effective in stimulating bowel movement and maintaining the normal environment of the intestinal tract.

Example 4: Effect of the Banana Fermentation Product of the Present Invention on Relieving Constipation Symptoms A trial of human subjects was conducted to confirm the effect of the banana fermentation product of the present invention on relieving constipation symptoms which proves the effect of the banana fermentation product on relieving constipation. First, a beverage containing 3 g of the banana fermentation product of the present invention was prepared and served as the experimental group. Eighteen subjects were recruited, and then, a beverage containing the banana fermentation product of the present invention was provided to each subject at a daily amount of 20 mL for one week. Each subject in the control group directly ate a banana every day for one week. The condition for relieving constipation symptoms was assessed by the eighteen subjects themselves via observing the stool (e.g., hard stool, little stool amount), rectum symptoms (e.g., decreased frequency of bowel movement, hard bowel movement, pain when having bowel movement, incomplete bowel movement, the urgency to have bowel movement but failed, rectal burning), and abdomen symptoms (e.g., stomachache, abdominal pain, stomach bloating) prior to and after drinking the beverage containing the banana fermentation product of the present invention. Scores of 0, 1, 2, 3 and 4 were used for representing the degree of symptoms, wherein 0 represents no symptom and 4 represents a very severe symptom. Results are shown in FIG. 4 and FIG. 5.

Figure 4:
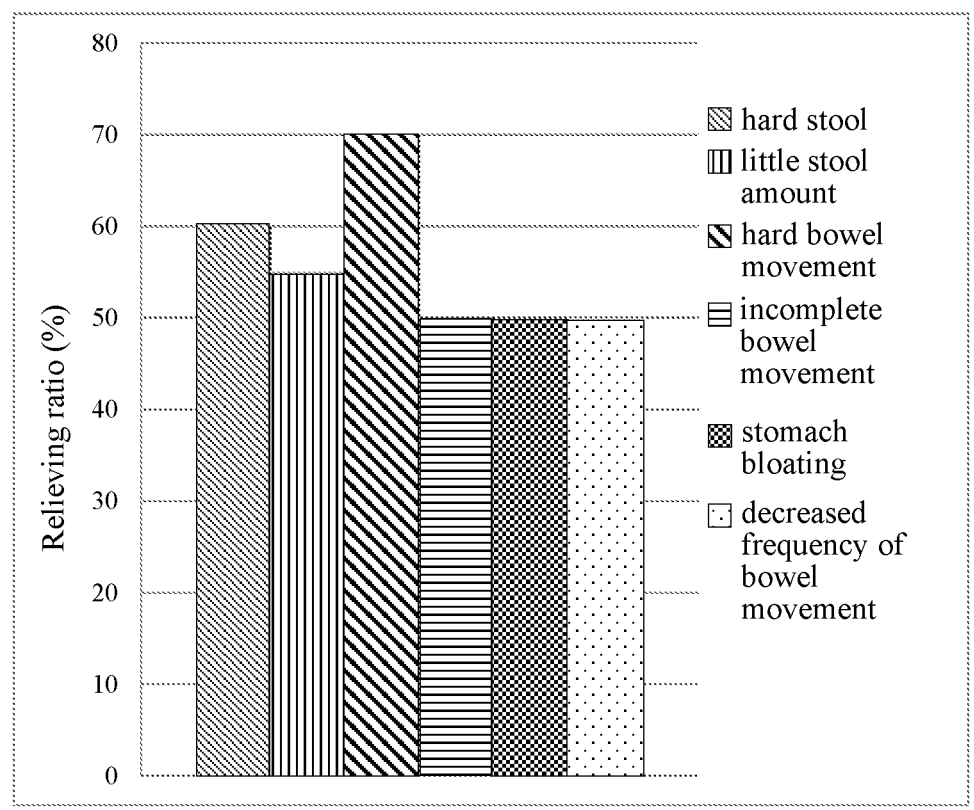
FIG. 4 is a diagram showing the effect of the banana fermentation product of the present invention on relieving constipation symptoms.
Figure 5:
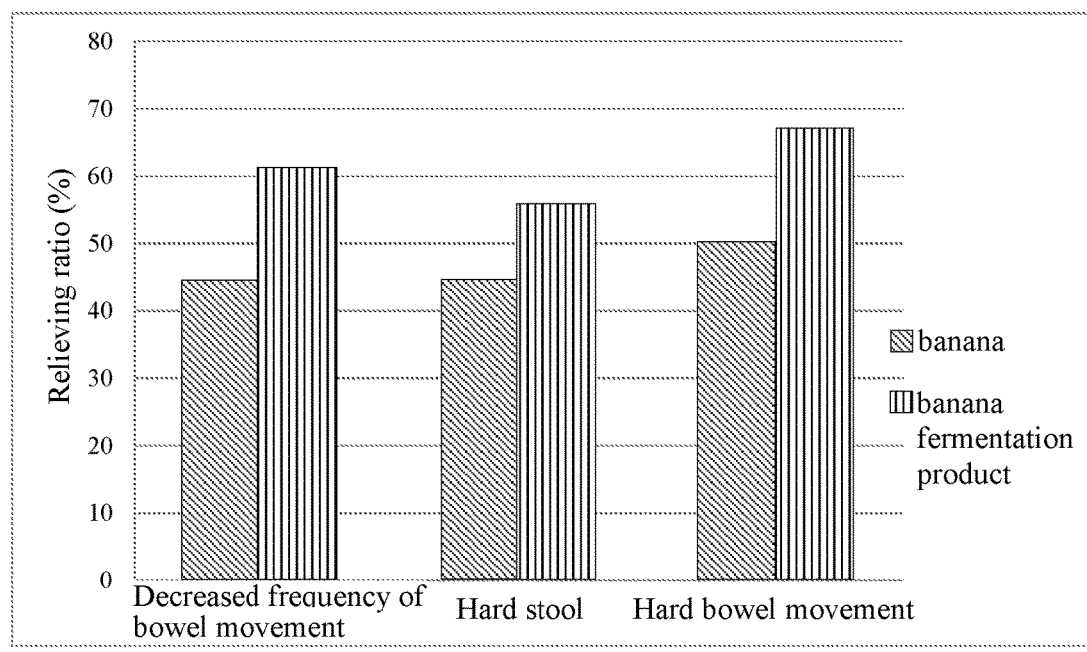
FIG. 5 is a diagram showing the effect of drinking the banana fermentation product in a beverage of the present invention on relieving constipation symptoms, as compared with directly eating bananas.

As shown in FIG. 4, the constipation symptoms such as hard stool, little stool amount, hard bowel movement, incomplete bowel movement, stomach bloating and decreased frequency of bowel movement were all relieved in more than 50% of the subjects. As shown in FIG. 5, as compared to the control group of eating a banana directly, the number of subjects that felt improved in the frequency of bowel movement, hard stool and hard bowel movement was significantly higher. These results indicate that the banana fermentation product of the present invention has an excellent effect on relieving constipation symptoms.

Given the above, the banana fermentation product of the present invention is obtained by subjecting a banana pulp juice to a pre-fermentation and then a post-fermentation, wherein the pre-fermentation is conducted in the presence of *Streptococcus thermophilus* TCI 633 (DSMZ 28121) and *Saccharomyces cerevisiae* (ATCC 4126T) and the post-fermentation is conducted in the presence of at least one of *Acetobacter aceti* (TISTR 102) and *Acetobacter aceti* (DSMZ 3508). The banana fermentation product of the present invention is effective in at least one of anti-oxidation, increasing the amount of probiotics, reducing the amount of bad bacteria and relieving constipation symptoms, wherein the constipation symptoms include at least one of hard stool, little stool amount, hard bowel movement, incomplete bowel movement, stomach bloating, and decreased frequency of bowel movement. Furthermore, inventors of the present invention found that, as compared to eating a banana directly, taking the banana fermentation product of the present invention is more effective in relieving constipation symptoms. Therefore, the banana fermentation product of the present invention can be used for providing a pharmaceutical or an edible composition in a variety of different dosage forms, via a natural, non-chemical synthesis process, and without causing side effects.

Deposit of Biological Material

Depository institute: DE Germany German Collection of Microorganisms and Cell Cultures (Deutsche Sammlung von Mikroorganismen and Zellkulturen GmbH, DSMZ); Address: Inhoffenstraße 7 B, 38124 Braunschweig, GERMANY; Date: 2013 Dec. 2; Accession number: DSMZ 28121.

BRIEF DESCRIPTION OF REFERENCE NUMERALS

Not applicable.

What is claimed is:

1. A banana fermentation product, which is obtained by subjecting a banana pulp juice to a pre-fermentation and then a post-fermentation, wherein the pre-fermentation is conducted in the presence of *Streptococcus thermophiles* DSMZ 28121 strain and *Saccharomyces cerevisiae* ATCC 4126T strain and the post-fermentation is conducted in the presence of at least one of *Acetobacter aceti* TISTR 102 strain and *Acetobacter aceti* DSMZ 3508 strain, and wherein, the pre-fermentation is conducted at 30° C.±1° C. for 72 hours, and the post-fermentation is conducted at 30° C.±1° C. for 21 days.

2. An edible composition comprising the banana fermentation product as claimed in claim 1.

3. The composition as claimed in claim 2, which is for at least one of relieving constipation symptoms, increasing the amount of probiotics in the intestinal tract, reducing the amount of bad bacteria in the intestinal tract, and anti-oxidation.

4. The composition as claimed in claim 3, wherein the composition is for relieving constipation symptoms and the constipation symptoms include at least one of hard stool, little stool amount, hard bowel movement, incomplete bowel movement, stomach bloating, and decreased frequency of bowel movement.

5. The composition as claimed in claim 3, wherein the composition is for increasing the amount of probiotics in the intestinal tract and the probiotic is at least one of *Lactobacillus acidophilus, Lactobacillus rhamnosus, Lactobacillus plantarum, Lactobacillus gasseri*, and *Lactobacillus brevis*.

6. The composition as claimed in claim 3, wherein the composition is for reducing the amount of bad bacteria in the intestinal tract and the bad bacterium is *Escherichia coli*.

7. A method for at least one of relieving constipation symptoms, increasing the amount of probiotics in the intestinal tract, and reducing the amount of bad bacteria in the intestinal tract, comprising administering to a subject in need an effective amount of the banana fermentation product as claimed in claim 1.

8. The method as claimed in claim 7, wherein the method is for relieving constipation symptoms and the constipation symptoms include at least one of hard stool, little stool amount, hard bowel movement, incomplete bowel movement, stomach bloating, and decreased frequency of bowel movement.

9. The method as claimed in claim 7, wherein the method is for increasing the amount of probiotics in the intestinal tract and the probiotic is at least one of *Lactobacillus acidophilus, Lactobacillus rhamnosus, Lactobacillus plantarum, Lactobacillus gasseri*, and *Lactobacillus brevis*.

10. The method as claimed in claim 7, wherein the method is for reducing the amount of bad bacteria in the intestinal tract and the bad bacterium is *Escherichia coli*.

11. A method for anti-oxidation, comprising administering to a subject in need an effective amount of the banana fermentation product as claimed in claim 1.

* * * * *